US000001312H

United States Statutory Invention Registration [19]

[11] Reg. Number: H1312

[43] Published: May 3, 1994

Coughlin et al.

[54] METHOD FOR THE PREPARATION OF GYK-DTPA

[75] Inventors: Daniel J. Coughlin, Robbinsville; Richard Wood, Rocky Hill, both of N.J.

[73] Assignee: Cytogen Corporation, Princeton, N.J.

[21] Appl. No.: 890,519

[22] Filed: May 28, 1992

[51] Int. Cl.[5] ..... A61K 37/02

[52] U.S. Cl. ..... 530/331; 530/345

[58] Field of Search ..... 530/331, 335, 336, 337, 530/324

[56] References Cited

U.S. PATENT DOCUMENTS

| | | | |
|---|---|---|---|
| 4,116,951 | 9/1978 | Wang | 260/112.5 |
| 4,148,788 | 4/1979 | Wang | 260/112.5 |
| 4,479,930 | 10/1984 | Hnatowich et al. | 424/1.1 |
| 4,622,420 | 11/1986 | Meares et al. | 562/443 |
| 4,668,503 | 5/1987 | Hnatowich | 424/1.1 |
| 4,741,900 | 5/1988 | Alvarez et al. | 424/85 |
| 5,057,313 | 10/1991 | Shih et al. | 424/85.91 |

FOREIGN PATENT DOCUMENTS

| | | |
|---|---|---|
| WO90/07713 | 7/1990 | PCT Int'l Appl. . |
| 2225579A | 6/1990 | United Kingdom . |
| 2241167A | 8/1991 | United Kingdom . |

OTHER PUBLICATIONS

Bodanszky, Int. J. Protein Res. (25) 449–474 (1985).

Alvarez et al., Antibody-Mediated Delivery Systems, John D. Rodwell, Ed., Marcel Dekker, Inc., New York, ch. 10. pp. 306–309 (1988).

Hnatowich et al., "The Preparation and Labeling of DTPA-Coupled Albumin", Int. J. Appl. Radiat. Isot. 33:327–332 (1982).

Krejcarek et al., "Covalent Attachment of Chelating Groups to Macromolecules", Biochem. Biophys. Res. Comm. 77:581 (1977).

Scheinberg et al., "Tumor Imaging With Radioactive Metal Chelates Conjugated to Monoclonal Antibodies", Sci. 215:1511–1513 (1982).

Sundberg et al., "Selective Binding of Metal Ions to Macromolecules Using Bifunctional Analogs of EDTA", J. Med. Chem. 17:1304 (1974).

Yeh et al., "Decomposition Rates of Radiopharmaceutical Indium Chelates in Serum", J. Radioanalytical Chem. 53:327 (1979).

*Primary Examiner*—Robert L. Stoll
*Assistant Examiner*—Joseph D. Anthony
*Attorney, Agent, or Firm*—Pennie & Edmonds

[57] ABSTRACT

Disclosed herein is a novel method for preparing a DPTA tripeptide-chelator. In particular, a method for preparing GYK-DTPA is described. The method disclosed herein is an improvement over the known methods of preparation based on the cost and labor savings of the present invention. The present invention utilizes t-butyloxycarbonyl (Boc) protecting groups to facilitate the polypeptide-chelator production.

2 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

Figure 1:
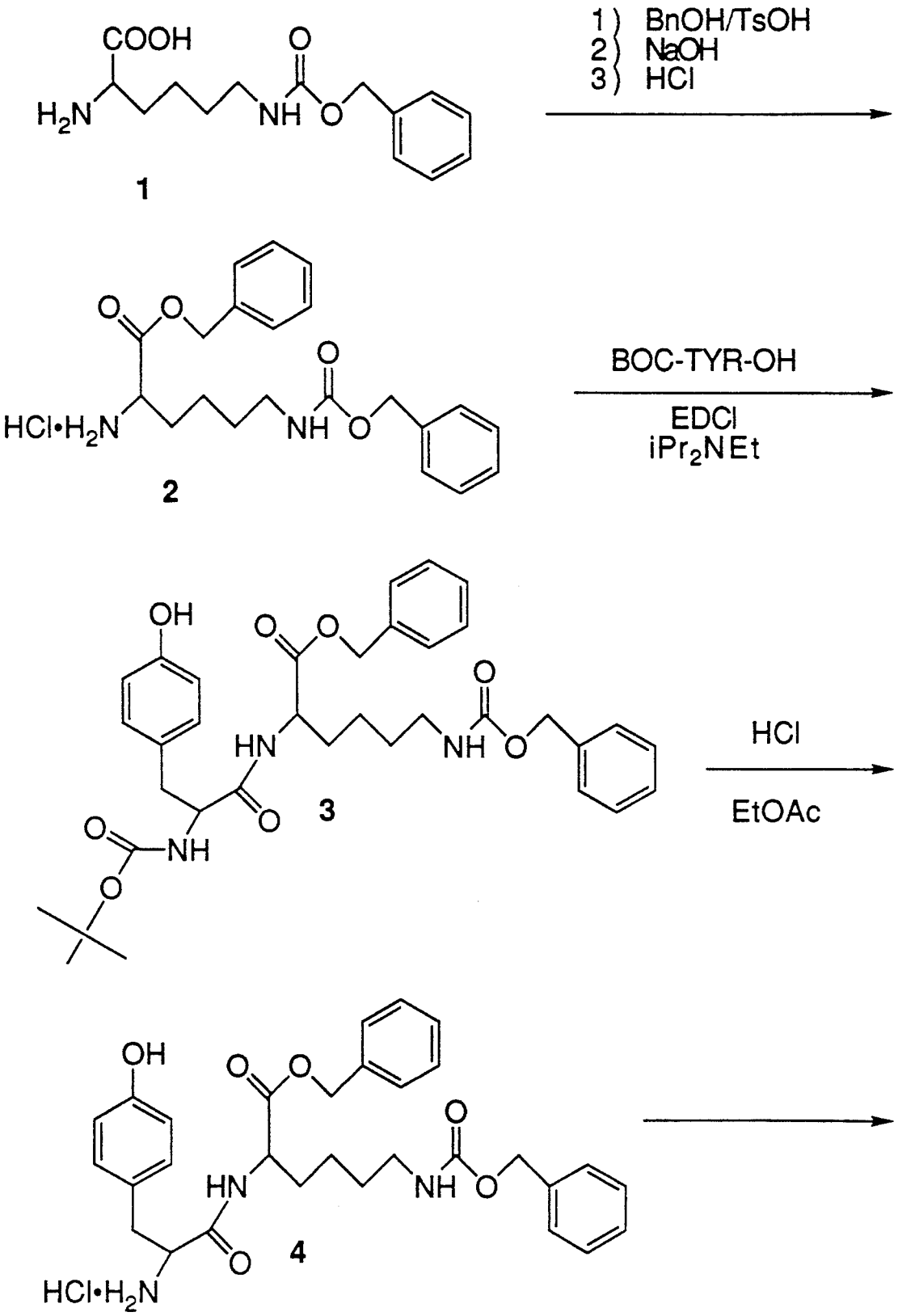

FIGURE 1 (con't)
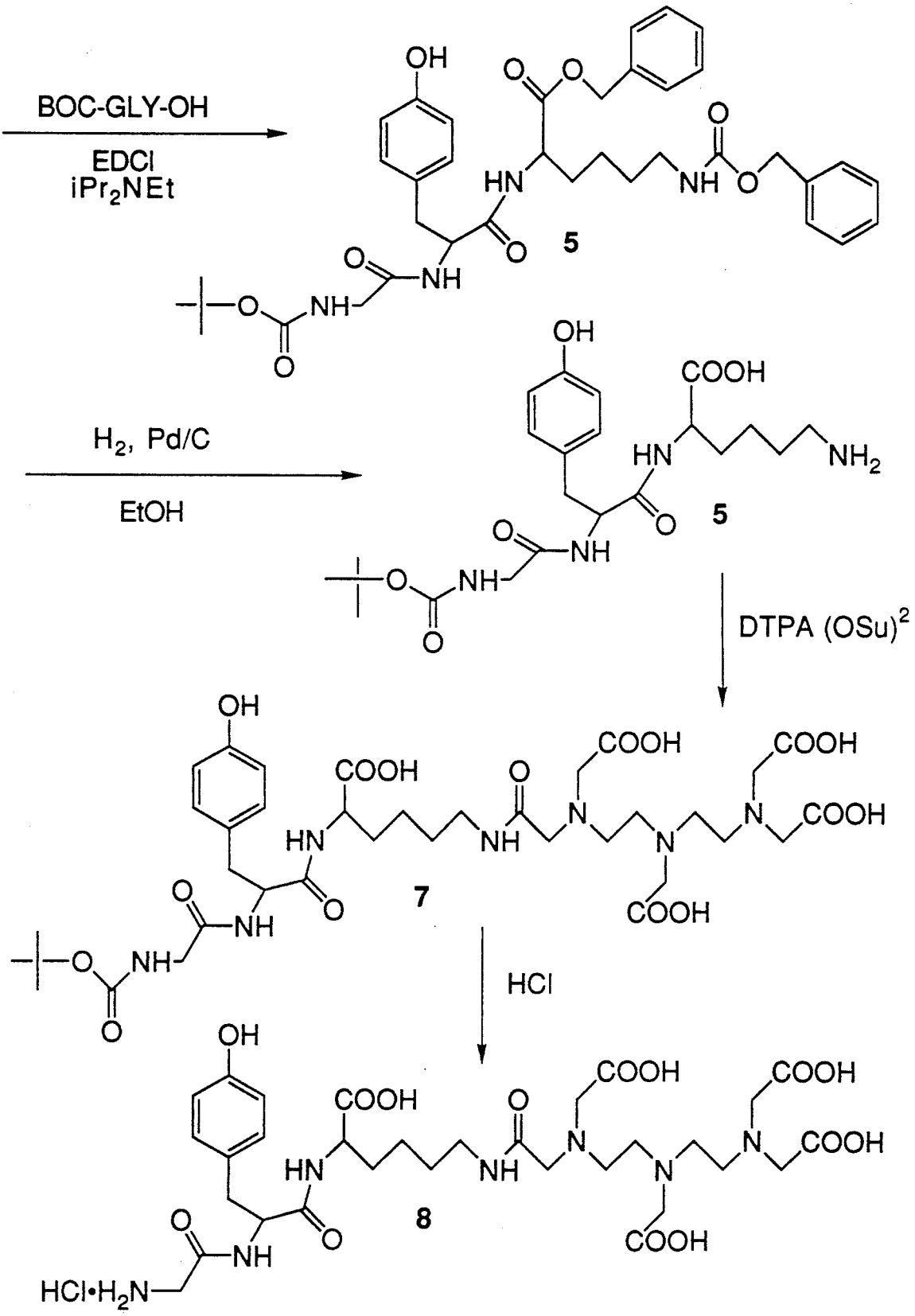

GYK-DTPA

METHOD FOR THE PREPARATION OF GYK-DTPA

TABLE OF CONTENTS

1. Field of the Invention
2. Background of the Invention
3. Summary of the Invention
4. Definitions
5. Brief Description of the Figures
6. Detailed Description of the Invention
6.1 Synthesis of GYK-DTPA
6.2. Uses for Tripeptide-DTPA
7. EXAMPLES
7.1. Materials and Methods
7.1. Example 1
Preparation of (N-ε-carbobenzyloxy)lysine benzyl ester hydrochloride 2
7.3 Example 2
Preparation of t-Butyloxycarbonyltyrosyl-(N-ε-benzyloxycarbonyl)lysine benzyl ester 3
7.4 Example 3
Preparation of Tyrosyl-(N-ε-benzyloxycarbonyl)lysine benzyl ester hydrochloride 4
7.5 Example 4
Preparation of (t-Butyloxycarbonyl)glycyl-tyrosyl-(N-ε-benzyloxycarbonyl)lysine benzyl ester 5
7.6 Example 5
Preparation of (t-Butyloxycarbonyl) glycyl-tyrosyl-lysine 6
7.7 Example 6
Preparation of (t-Butyloxycarbonyl)glycyl-tyrosyl-(N-ε-diethylenetriamine-pentaccetic acid) lysine 7. Method A
7.8 Example 7
Preparation of (t-Butyloxycarbonyl)glycyl-tyrosyl-(N-ε-diethylenetriaminepentaccetic acid)lysine 7 from GYK-DTPA. Method B
7.9 Example 8
Preparation of glycyl-tyrosyl-(N-ε-diethylenetriamine-pentaacetic acid) lysine 8Method C
7.10 Example 9
Preparation of glycyl-tyrosyl-(N-ε-diethylenetriamine-pentaacetic acid) lysine 8. Method D

1. FIELD OF THE INVENTION

The present invention relates to a novel method for preparing a polypeptide-chelator. More particularly, the invention relates to a novel method for preparing the tripeptide-chelator, glycyl-tyrosyl-(N-ε-diethylenetriaminepentaacetic acid)lysine ("GYK-DTPA") or glycl-tyrosyl-(N-ε-diethylenetriaminepentaacetic acid-)lysine hydrochloride ("GYK-DTPA HCl") with the use of t-butyloxycarbonyl (Boc) protecting groups.

Chelators are organic compounds that are able to donate electrons and combine by coordinate bonding with a metal ion to form structures termed chelates or chelation complexes. There are many known chelators which may be used to form conjugates with a variety of proteins, peptides or glycoprotein substances. Polypeptide-chelators are just one example of chelator intermediates which can be used to covalently link a chelator in order to form a conjugate. Polypeptide chelators may also be used alone to form polypeptide complexes with metal ions. More particularly, GYK-DTPA is a polypeptide-chelator which is useful in preparing such metal ion complexes. These complexes are useful for the delivery of metal ions which may be radioisotopes or another detectable ion, to target sites in vitro or in vivo.

2. BACKGROUND OF THE INVENTION

A method of synthesis of a particular polypeptide-chelator described herein, GYK-DTPA (glycyl-tyrosyl-(N-ε-diethylenetriaminepentaacetic acid)lysine), has been disclosed in U.S. Pat. No. 4,741,900 to Alvarez et al. This synthesis however, depends upon the utilization of the base-cleavable 9-fluorenylmethyloxycarbonyl (Fmoc) protecting group. This strategy has several disadvantages. First, the process is costly due to the use of the expensive Fmoc protecting group and to the labor-intensive preparative HPLC chromatographic purification of end products required to obtain a purified homogeneous product. Secondly, premature loss of the Fmoc group and byproduct formation during scheduled Fmoc removal and DTPA coupling are problematic. The lack of easily purified intermediates necessitates the accumulation of side products, and a preparative high-pressure liquid chromatographic separation is required. In an attempt to address these shortcomings, a new synthesis of GYK-DTPA utilizing the acid-cleavable t-butyloxycarbonyl (Boc) amino protection was devised.

According to U.S. Pat. No. 4,741,900 to Alvarez et al., GYK-DTPA was synthesized as follows: the initial peptide reactant N-Fmoc-glycyl-(O-benzyl-tyrosyl-(ε-N-carbobenzyloxy) lysine was prepared according to standard solid phase synthetic methods described by Baranz and Merrifield. In The Peptides, Vol. 2, Gross and Meienhoffer (ed.), Acad. press, New York, pp. 3–385, 1980. The derivatized peptide was cleaved from the resin and partially deblocked by bubbling hydrogen bromide (HBr) gas through a suspension of the reaction mixture in trifluoracetic acid containing methoxybenzene (a fifty-fold molar excess over tyrosine) for 60 minutes at room temperature. The resin was removed by filtration and the filtrate evaporated to dryness. The residue was dissolved in a minimum amount of methanol, and the product precipitated with ether and used without further purification.

One mole N-Fmoc-glycyl-tyrosyl-lysine in DMF was reacted with 1 mole DTPA mixed anhydride prepared as described in Krejcarek et al., [Biochem. Biophys. Res. Comm. 77:581–585 (1977)] in which diisopropylethylamine was used for 30 minutes at −15° C., and then maintained at room temperature for 1 hour. The solvent was removed by rotary evaporation and the oily residue dissolved in a small aliquot of DMF. Distilled water was added to precipitate the Fmoc-GYK-DTPA produced. The Fmoc group was removed by addition of an equal volume of 40% dimethylamine in DMF to a solution of Fmoc-GYK-DTPA in DMF, followed by incubation for 30 minutes at room temperature. The solvent was evaporated to dryness and the residue taken up in distilled water. The crude product was purified by extraction with ethyl acetate and the resulting aqueous solution of GYK-DTPA was lyophilized to dryness.

More recently, Alvarez et al., [in Antibody-Mediated Delivery Systems, John D. Rodwell, Ed., Marcel Dekker, Inc., New York, (1988), ch. 10, pp. 306–309] described the synthesis of GYK-DTPA as summarized below. GYK-DTPA was prepared starting with a commercially-available dipeptide, glycyl-tyrosine. The amino terminus of the glycyl-tyrosine starting material was protected by reaction with 9-fluorenylmethyl succinimidyl carbonate (Fmoc-OSu), to provide the corresponding urethane. Subsequently, a peptide-coupling reaction was performed with N-ε-benzyloxycarbonyl-lysine methyl ester (H-Lys(ε-CBZ)-OMe) utilizing the coupling reagents dicyclohexylcarbodiimide and 1-hydroxybenzotriazole (DCC/HOBt). The resulting tripeptide derivative was fully-protected GYK. The urethane protection at the ε-amino group of the lysine side-chain was cleaved through the agency of hydrobromic acid in acetic acid, providing the Fmoc-GYK-OMe hydrobromide salt, whose amino and carboxy termini remain protected.

The N-Fmoc-GYK(OMe)-HBr and diisopropylethylamine in dry DMF were then reacted with a DTPA mixed anhydride which was prepared by modification of the method of Krejcarek et al. [Biochem. Biophys. Res. Comm. 77: 581–585 (1977)] at about 0° C. for about two hours. The reaction mixture was evaporated and the crude Fmoc-GYK-(OMe)-DTPA solid was dissolved in DMF and 40% dimethylamine in water to remove the Fmoc protecting group. The methyl protecting group was then removed by saponification in 1N NaOH. The final product, GYK-DTPA was isolated using preparative C-18 reverse phase HPLC using a gradient of 0.1% TFA and acetonitrile.

As a result of the Fmoc procedure's multiple problems: high cost, labor-intensive preparative HPLC chromatographic purification of the end product, the potential premature loss of the Fmoc group and by-product formation during Fmoc removal and DTPA coupling, the lack of easily purified intermediates necessitating the accumulation of side products and the requirement of preparative high-pressure liquid chromatographic separation there remains a need for, a new method for synthesis to remedy and/or avoid these problems.

Other references which describe or relate to o coupling of chelators, including DTPA, to proteins and/or antibodies include the following: U.S. Pat. No. 4,479,930 to Hnatowich et al. describes reaction of an amine of a polypeptide or protein with a dicyclic dianhydride chelator of the formula

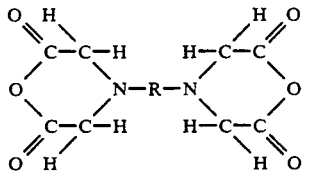

where R is a linker from 1–25 carbon atoms and which can include nitrogen and/or carboxyl or other groups which do not denature proteins or peptides. The chelators attached to amines include the dicyclic dianhydride of DTPA (see also, Hnatowich, 1982, Int. J. Appl. Radiat. Isot. 33:327–332), U.S. Pat. No. 4,668,503 also to Hnatowich describes labeling of the amine, polypeptide or protein chelator conjugates with Technetium-99 m.

British Patent Application Publication Nos. GB 222579 published Jun. 6, 1990 and GB 224167 published Aug. 28, 1991 describe conjugates of somatastatin peptide analogues and chelating groups including such as DTPA, EDTA, substituted EDTA, DTPA, e.g., p-isothiocyanato-benzyl EDTA or -DTPA, and groups derived from macrocyclic ligands such as 1,4,7,10-tetraazacyclododecane-N,N′,N″,N‴-tetra-acetic-D-Phe acid, etc. A particular example includes DTPA-D Phe-Cys-Phe-D-Thr-Lys-Thr-Cys-Thr-OH in which it appears the DTPA is attached to the somatastatin analogue according to a method similar to or the same as the method described by Hnatowich.

Other attempts to develop chelating agents useful for attaching a metal or metal ion to a protein or glycoprotein have included the following. Sundberg et al., 1974, J. Med. Chem. 17:1304 described a complex, multi-step synthesis of 1-(p-benzyldiazonium)-EDTA. EDTA derivatives may not be as useful as DTPA derivatives. Yeh et al., 1979, J. Radioanalytical Chem. 53:327 described a method using 1-(p-carboxymethoxybenzyl)-EDTA which had the same disadvantages as that of Sundberg. Krejcarek et al., 1977, Biochem. Biophys. Res. Comm. 77:581 and more recently Scheinberg et al., 1983, Sci. 215:1511–1513 described attachment of a glycoprotein or protein to a metal ion using a carboxycarbonic anhydride of DTPA. The reaction schemes used by Krejcarek and Scheinberg are not selective for derivatizing a single or particular carboxyl group of the DTPA and can result in undesirable cross-linking when the DTPA derivative is attached to a protein or polypeptide or alternatively can result in undefined DTPA linked products.

It is an object of the present invention to provide a novel synthesis which provides the benefit of using inexpensive starting materials, thereby avoiding the costly use of dipeptides and Fmoc protection reagents.

It is a further object of the present invention to utilize inexpensive reagents and solvents throughout the process. In addition, most of the solvents used in this novel method are volatile and are amenable to solvent recovery, thereby further reducing cost. Another object of the present invention is to minimize the use of DMF which is undesirable.

It is a further object of the present invention to provide stable intermediates which can be easily isolated in excellent purity. The ability to purify these intermediates obviates the need for extensive end-product purification.

In addition it is a further object of the present invention to eliminate the need for a preparative HPLC to purify intermediates or final products.

3. SUMMARY OF THE INVENTION

According to the present invention, a novel process for preparing GYK-DTPA and/or GYK-DTPA HCl utilizing acid-cleavable t-butyloxycarbonyl (Boc) protecting groups is described. In one embodiment of the present invention, an inexpensive starting material such as a single amino acid residue is used. The starting amino acid residue possessing suitable side chain protection is protected with a suitable protecting group in order to form a carboxy and side chain protected amino acid. This protected amino acid is then reacted with another amino acid residue which has a t-butyloxycarbonyl (Boc) protecting group in the presence of a suitable coupling agent to form a dipeptide having a Boc protected amine terminus and a carboxy terminal ester.

The multiply protected dipeptide is then stripped of its Boc protecting group by reaction with an acid in a suitable solvent to form a salt of the dipeptide. The salt of the dipeptide is then reacted with another (Boc) protected amino acid residue in the presence of a suitable coupling agent and base to form a tripeptide with a Boc protected amino terminus and a carboxy terminal ester. It is preferred that the carboxy terminal amino acid residue is lysine.

Upon obtaining the desired tripeptide, the tripeptide is treated with appropriate reagents to remove two of the protecting groups to form a partially deprotected polypeptide having a Boc protected amino terminus. According to a preferred embodiment, the tripeptide is reacted with $H_2$ in the presence of a catalyst to remove benzyl ester and side chain carbobenzyloxy protecting groups. Upon partial deprotection, the polypeptide is reacted with a suitable DTPA derivative at the side chain to form a Boc-protected tripeptide-DTPA. Finally the Boc protected tripeptide-DTPA is reacted with an acid to remove the Boc protecting group from the amino terminus to form the desired tripeptide-DTPA in its acid salt form.

The GYK-DTPA prepared by the method of the invention is particularly useful for forming conjugates and metal ion complexes for a variety of in vitro applications as well as in vivo therapeutic and diagnostic applications known to those skilled in the art.

4. DEFINITIONS

As used throughout the present application, the term "suitable solvent" is meant to encompass solvents which are appropriate for the reactants and reagents used in each corresponding step which will be apparent to one skilled in the art. Examples of preferred solvents used in the present process include, but are not limited to, toluene, ethyl acetate, methanol, ethanol, isopropyl alcohol, dioxane, dimethoxyethane, dimethlyformamide methylene chloride, tetrahydrofuran, etc.

As used throughout the present application, the term "suitable coupling agent" is intended to encompass an agent which is capable of facilitating the coupling of two amino acid residues in order to form an amide bond. Such suitable coupling agents are selected from the group consisting of 1-ethyl-3 -(3-dimethylaminopropyl)-carbodiimide ("EDCI"), dicyclohexylcarbodiimide ("DDC"), carbonyl dimidazole, 1-ethoxycarbonyl-2-ethyloxy-1,2-dihydroquinoline ("EEDQ"), benzotriazol-1-yloxytris (dimethylamino)phosphonium hexafluorophosphate ("BOP"), etc.

As used throughout the present application, the term "suitable catalyst" is intended to encompass a catalyst which is used in hydrogenation reaction such as known by those skilled in the art. Examples include, but are not limited to, palladium on carbon, platinum on carbon, platinum oxide etc. In a preferred embodiment of the present invention, the term "suitable catalyst" refers to palladium on carbon.

As used throughout the present application, the term "suitable acid" is meant to encompass inorganic and organic acids, as known to those skilled in the art which are appropriate for the transformation which is to occur. Examples of suitable acids as used in the present invention include, but are not limited to, gaseous HCl, aqueous HCl, HCl in an organic solvent, trifluoroacetic acid, methane sulfonic acid, benzenesulfonic acid, p-toluene sulfonic acid, etc. In a preferred embodiment of the present invention, "suitable acid" refers to gaseous HCl dissolved in a suitable solvent.

5. BRIEF DESCRIPTION OF THE FIGURES

The invention may be more fully understood by reference to the following detailed description and examples as well as the appended figures in which:

FIG. 1 schematically represents a novel method for synthesizing Glycyl-tyrosyl-(N-ϵ-diethylenetriaminepentaacetic acid)lysine.

Figure 2:
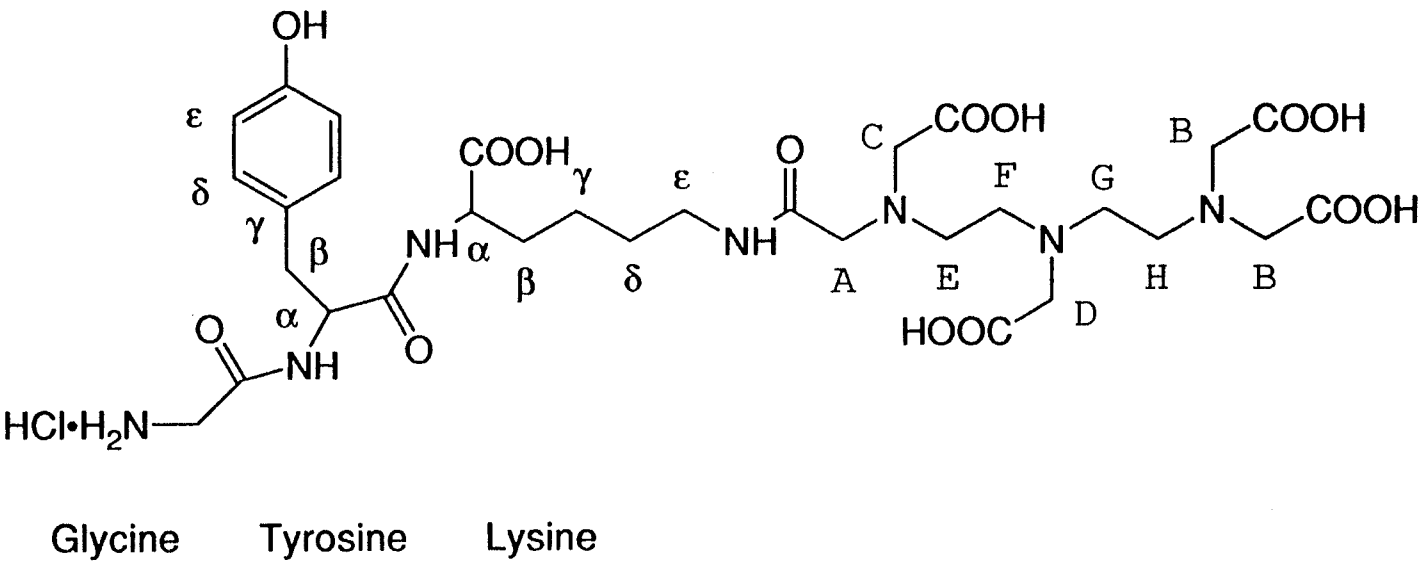

FIG. 2 schematically represents GYK-DTPA. Greek letter labels refer to standard peptide nomenclature. Arabic labels denote identification of nonequivalent methylene carbons in the DTPA backbone.

6. DETAILED DESCRIPTION OF THE INVENTION

The present invention is directed to a novel method for preparing a tripeptide-DTPA chelator utilizing acid-cleavable t-butyloxycarbonyl (Boc) protecting groups. The tripeptide comprises the amino acid residues, glycine, tyrosine and lysine, preferably the carboxy terminal amino acid residue is a lysine. In a particular embodiment of the present invention, an inexpensive starting material such as a single suitable amino acid residue is used. The preferred starting amino acid is lysine, having a protected ϵ-amine group. This amino acid residue protected with a suitable group in the presence of a suitable solvent to form a carboxy and side chain protected amino acid. The resulting protected amino acid residue is reacted with another amino acid residue having a t-butyloxycarbonyl (Boc) protecting group, in the presence of a suitable coupling agent, to form a dipeptide having a Boc protected amine terminus and a protected side chain and carboxy terminus. Boc protected amino acid residues are prepared by methods known to those skilled in the art. An example of one such preparation includes, for example, McKay et al., [J. Amer. Chem. Soc. 79, 4686 (1957)].

The Boc-protecting group is then removed from the protected amine group by reacting the dipeptide with a suitable acid in a suitable solvent to form a suitable salt of the dipeptide.

The salt of the dipeptide is then reacted with (Boc) protected amino acid residue in the presence of a suitable coupling agent to form a tripeptide with a Boc protected amine terminus and a protected carboxy terminus and side chain.

The tripeptide is treated with an appropriate reagent to remove two of the suitable protecting groups to form a deprotected tripeptide having Boc protection at the amino terminus. According to a preferred embodiment; the tripeptide is reacted with $H_2$ in the presence of a catalyst to remove benzyl ester and carbobenzyloxy protecting groups. Both the ease of removal as well as the multiple nature of the removal of the protecting groups are benefits derived from the novel method described herein.

Upon side chain deprotection, the tripeptide can be reacted with the bis-N-hydroxysuccinimide ester of DTPA (DTPA-OSu ester) to form the desired tripeptide-DTPA penultimate adduct. Finally the tripeptide-DTPA penultimate adduct is deprotected by reaction with an acid to form the desired unprotected tripeptide-DTPA in its acid salt form.

In another embodiment described herein, the inexpensive starting material used is a N-ϵ-carbobenzyloxy lysine. This starting material has an unprotected carboxy terminus and one protected and one unprotected amine group. This starting material is reacted with a suitable alcohol in the presence of a suitable solvent to form a carboxy protected N-ϵ-carbobenzyloxy lysine. The carboxy protected N-ϵ-carbobenzyloxy lysine is then reacted with a tyrosine residue having a t-butyloxycarbonyl (Boc) protecting group in the presence of a suitable coupling agent to form a dipeptide Boc-tyrosine-(N-ϵ-CBZ)-lysine benzyl ester, i.e., having a Boc protected amine terminus and an ester protected carboxy terminus. Any suitable coupling agent known to those skilled in the art can be used such as DDC or EDCI. The preferred coupling agent is EDCI. The Boc protecting group is then removed from the amine terminus (while the carboxy and side chain protecting groups remain intact) by treatment with a suitable acid in a suitable solvent which forms an acid salt of the dipeptide. The preferred acid for this step is gaseous HCl in ethyl acetate, however, other acids and solvents may be used as appropriate for the transformation.

This is followed by reacting the hydrochloride salt of the dipeptide with a glycine residue having a Boc protecting group in the presence of a suitable coupling agent and base to form a tripeptide having a Boc-protected amine terminus and a protected carboxy terminus. The preferred coupling agent is EDCI which is used in a suitable solvent such as methylene chloride. The tripeptide is then treated with hydrogen gas in the presence of a suitable catalyst in a suitable solvent in order to remove the carboxy and side chain protection and to form a partially deprotected tripeptide (Boc-GYK-OH). The preferred catalyst is palladium on carbon. Suitable solvents include lower alcohols such as methanol or ethanol. The preferred solvent is ethanol. The Boc-GYK tripeptide is then reacted with the chelator to form a Boc-protected GYK-DTPA. Finally, the Boc-protected GYK-DTPA is reacted with an acid to remove the Boc protecting group from the Boc protected amine terminus to form a GYK-DTPA acid salt.

The process of the invention is uniquely designed such that this step in fact deprotects two functionalities simultaneously leading to greater cost effectiveness and ease.

6.1 SYNTHESIS OF GYK-DTPA

In a preferred embodiment of the present invention, a protected N-ϵ-carbobenzyloxy lysine 1 having an unprotected carboxy and amine terminus is reacted with benzyl alcohol in toluene at about 110°--about 120° C. in order to form a carboxy protected N-ϵcarbobenzyloxy lysine ester 2. Subsequently, a tyrosine residue having a Boc protecting group is then reacted with the carboxy protected N-ϵ-carbobenzyloxy lysine through a 1-ethyl-3-(3-dimethylaminopropyl)-carbodiimide mediated coupling to form a dipeptide Boc tyrosine (N-ϵ-CBZ) lysine benzyl ester having a Boc protected amine terminus and protected carboxy terminus 3. This operation, unlike the coupling performed in the Fmoc-based approach, requires no auxiliary reagents, such as HOBt. The Boc protecting group is then conveniently removed from the Boc protected amine terminus by treatment with HCl in ethyl acetate to form a hydrochloride salt of the tyrosine-lysine dipeptide 4. The reaction is preferably carried out using gaseous HCl in ethyl acetate at a temperature from about 0° C. to about 25° C. However, a temperature of about 0° C. is preferred. The hydrochloride salt of the dipeptide is obtained in a sufficiently high purity which eliminates the need for further purification at this step.

The production of the hydrochloride salt of the dipeptide is followed by a reaction with a glycine residue having a Boc protecting group through a 1-ethyl-3-(3-dimethylaminopropyl)-carbodiimide mediated coupling (EDCI). The reaction product is a tripeptide (GYK) having a Boc protected amine group 5. The tripeptide (GYK) is then reacted with hydrogen gas in the presence of a palladium on carbon in an ethanol solvent at a temperature sufficient to form a partially deprotected tripeptide Boc-GYK-OH 6. Again, the synthesis is designed to allow for the removal of two of the protecting groups simultaneously and easily. The tripeptide is formed in high yield as a crystalline solid. The protected trieeptide intermediate may optionally be further purified by recrystallization. The partially deprotected tripeptide Boc-GYK is then reacted through an acylation with diethylenetriaminepentaacetic disuccinimdyl ester to form Boc-GYK-DTPA 7. The product is formed in high yield and may optionally be purified using successive recrystallizations from an isopropyl alcohol/methanol mixture. Finally, the Boc protecting group is removed from the Boc protected amine terminus with aqueous HCl 8.

Crude GYK-DTPA may optionally be passed through a low-pressure glass C18 column.

It is possible that the column step be avoided if the penultimate intermediate 7 is prepared in very high purity, e.g. by recrystallization.

There are therefore two methods of rroducing GYK-DTPA of acceptable purity by this approach: 1) attaining high purity in the penultimate intermediate 7 by recrystallization, 2) purifying end product 8 with low pressure C18 chromatography.

The overall Boc approach offers higher yield throughout, since there is no need for the high pressure liquid chromatographic purification at the end. The yields are high and product purification requires simple synthetic operations.

6.2. USES FOR TRIPEPTIDE-DTPA

As mentioned above the tripeptide-chelators prepared by the method of the invention are useful in attaching metal ions, such as radioisotopes, to proteins, peptides or glycoprotein substances. As used in the present application, the term a "protein, peptide or glycoprotein substance" is intended to encompass proteinaceous substances, including non-glycosylated proteins, glycoproteins, proteoglycans, etc., as well as peptidyl, polypeptidyl and glycopeptidyl substances. As such, the term includes polyclonal serum immunoglobulins, monoclonal antibodies, fragments of monoclonal antibodies having at least a portion of an antigen binding region including such as Fv, $F(ab')_2$, Fab, and Fab' fragments, single chain antibodies, chimeric or humanized antibodies, complementarily determining regions (CDRs), etc., serum complement components, enzymes, cell surface histocompatibility antigens, cell surface receptors, peptide or proteinaceous hormones, proteins or peptides which bind to cellularreceptors, and molecular recognition units as that term is described in International Publication No. WO 90/07713 published Jul. 12, 1990, incorporated herein by reference. Attachment of the tripeptide-chelator to a protein, peptide or glycoprotein substance forms a conjugate. The conjugates are useful to prepare metal ion complexes for use as in vivo therapeutics as well as in vivo and in vitro diagnostics. Specifically, the complexes may be used for detection or delivery of labeled metal ions in. for imaging of specific tissues, for therapy at specific tissue or organ sites and immunological assays as described, for example, by Alvarez et al. U.S. Pat. No. 4,741,900. Attachment of the tripeptide-chelator to a protein, peptide or glycoprotein substance forms a conjugate. Chelation of a metal ion to the conjugate forms a metal ion complex.

In order to more fully illustrate the nature of the invention and the manner of practicing the same, the following examples are provided, which are not to be construed as limiting the remainder of the disclosure or the scope of the invention in any way whatsoever.

7.1. EXAMPLES

7.1. Materials and Methods

Starting materials were purchased from Aldrich Chemical Co., Sigma Chemical Co., Vega Chemical Co. or Bachem, Inc. and were used without purification. Melting points were determined on an Electrothermal Melting Point Apparatus and are uncorrected. Nuclear Magnetic Resonance experiments were performed on a Varian Gemini 300 at 300 MHz (proton) and 75 MHz (carbon). Microanalyses were performed by Atlantic Microlab, Inc. HPLC analyses were performed on a Waters 3000 HPLC or a Rainin Rabbit-HP using one of the following systems: System A: Waters NovaPak C18 HPLC column, utilizing a linear gradient from 0% A: 100% B to 100% A: 0% B over fifteen minutes; System B: Waters NovaPak C18 HPLC column, utilizing a linear gradient from 0% A: 100% B to 80% A: 20% B over fifteen minutes. System C: Waters NovaPak C18 HPLC column, utilizing a linear gradient from 20% A: 80% B to 0% A: 100% B over fifteen minutes; System D: Waters NovaPak C18 HPLC Column, elution with Solvent B for five minutes then utilizing a linear gradient from 100% B: 0% A to 20% B: 80% A over fifteen minutes; System E: Millipore NovaPak C8 HPLC Column, utilizing a linear gradient from 0% A: 100% B to 80% A: 20% B over fifteen minutes; Solvent A=$CH_3CN$, Solvent B=0.1% $CF_3COOH$ in water. Mass spectra were determined at the Yale University School of Medicine.

7.2. EXAMPLE 1

Preparation of (N-ϵ-carbobenzyloxy)lysine benzyl ester hydrochloride 2

A suspension of 48.69 g (174 mmol) of (N-ϵ-carbobenzyloxy)lysine (Bachem, Inc.) in a solution of p-toluenesulfonic acid (33.04 g, 174 mmol) in toluene (500 mL) and benzyl alcohol (330 mL) was heated to reflux under a Dean-Stark separator. As reaction progressed the solution became homogeneous. Reflux was continued for 22 hr, at which time 6.6 mL of water (106% of theoretical) had collected. The bulk of the toluene was distilled out of the reaction mixture at atmospheric pressure, then the solution was concentrated by distillation under reduced pressure until 750 mL (90%) of the mixture of solvents had been collected. The residue was diluted with EtOAc (800 mL), chilled in an ice bath, and treated with water (200 mL), 2N NaOH (87 mL), and brine (200 mL). A small amount of flocculent precipitate was removed by filtration, and the pH of the aqueous phase was adjusted to 10 with 2N NaOH. The organic phase was washed with brine, dried over $MgSO_4$, filtered to remove dryinq agent, and cooled to ice-bath temperature. Anhydrous HCl was bubbled through the solution for 5 minutes, resulting in the formation of a copious white precipitate. Stirring was continued for an additional 5 minutes, then $N_2$ was bubbled through the mixture for 20 minutes to dispel HCl. The product was collected by filtration and dried under vacuum over $P_2O_5$ to afford a white solid. $^1H$ NMR (CF3COOD) δ 1.38 (m, 2H), 1.58 (m, 2H), 2.15 (m, 2H), 3.30 (m, 2H), 4.41 (m, 2H), 5.31 (s, 2H), 5.40 (AB, J=5.6 Hz, 2H), 7.42 (m, 10 H).

7.3 EXAMPLE 2

Preparation of t-Butyloxycarbonyl-tyrosyl-(N-ϵ-benzyloxycarbonyl)lysine benzyl ester 3

A suspension of lysine derivative 2 (40.65 g, 100 mmol) in $CH_2Cl_2$ (350 mL) was treated with diisopropylethylamine (17.5 mL, 100 mmol) and the resulting solution was cooled to 0° C. N-t-Butyloxycarbonyl tyrosine (Vega, 28.10 g, 100 mmol) was added in one portion, followed by 1-ethyl-3-(3-dimethylaminopropyl)carbondiimide (Sigma, 21.09 g, 100 mmol). The resulting suspension cleared to a homogeneous solution upon stirring at 0° C. After 18 h, the reaction solution was washed with saturated $NaHCO_3$, then 1N HCl, and dried ($MgSO_4$) and concentrated to give 62.06 g (99%) of a white solid. Recrystallization from hot ethanol/water returns 90.2% : Purity 99.7% (HPLC, System A); MP 68°–70° C.; $^1H$ NMR (DMSO-$d_6$) δ1.28 (s, 9H), 1.33 (m, 4H), 1.67 (m, 2H), 2.54 (m, 1H), 2.79 (m, 1H), 2.94 (m, 2H), 4.10 (m, 1H), 4.28 (m, 1H), 4.98 (s, 2H), 5.10 (s, 1H), 6.62 (d, J=8.4 Hz, 2H), 6.77 (d, J=8.6 Hz, 1H, exchangeable with $D_2O$), 7.02 (d, J=8.4 Hz, 2H), 7.20 (m, 1H, exchangeable with $D_2O$), 7.33 (m, 10H), 8.24 (d, J=7.8 Hz, exchangeable with $D_2O$), 9.12 (s, 1H, exchangeable with $D_2O$); $^{13}C$ NMR (DMSO-$d_6$) δ 22.4, 27.9, 28.8, 30.4, 36.8, 42.1, 43.2, 52.0, 53.5, 65.1, 65.8, 78.1, 115.0, 127.7, 127.8, 127.9, 128.1, 128.4, 128.5, 130.2, 136.1, 137.5, 156.1, 156.3, 169.2, 171.6, 171.9; FAB+ MS m/z 534.5 (M+H - $Me_3CO_2C$).

Anal. Calcd for $C_{35}H_3N_3O_8H_2O$: C, 64.50; H, 6.91; N, 6.76. Found: C, 64.50; H, 6.95; N, 6.56.

7.4 EXAMPLE 3

Preparation of Tyrosyl-(N-ϵ-benzyloxycarbonyl)lysine benzyl ester hydrochloride 4

A suspension of the tyrosyl-lysine derivative 3 (59.71 g, 96.15 mmol) in EtOAC (750 mL) was cooled to 10° C. and anhydrous HC1 was bubbled through for 20 min. Isopropyl alcohol (500 mL) was added and the resulting homogeneous solution was stored at rt for one hour. Solvents were removed in vacuo to provide a white solid: Purity 93.3% (HPLC, System B); MP 135°–138° C.; $^1H$ NMR (DMSO-$d_6$) δ 1.37 (m, 4H), 1.70 (m, 2H), 2.78 (m, 1H), 2.99 (m, 3H), 4.00 (br s, 1H), 4.32 (m, 1H), 5.0 (s, 2H), 5.14 (m, 2H), )6.69 (d, J=8.5 Hz, 2H), 7.07 (d, J=8.5 Hz, 2H), 7.32 (m, 10 H), 8.16 (br s, 2H, exchangeable with $D_2O$), 9.03 (d, J=7.1 Hz, 1H, exchangeable with $D_2O$), 9.41 (s, 1H, exchangeable with $D_2O$); $^{13}C$ NMR (DMSO-$d_6$) δ 22.4, 28.9, 30.5, 36.0, 52.2, 53.4, 65.1, 66.0, 115.2, 124.6, 124.7, 127.6, 127.8, 127.9, 128.1, 128.3, 128.4, 130.4, 130.5, 135.8, 137.2, 156.0, 156.5, 168.3, 171.2; FAB+ MS m/z 534.5 (M+H, Cl. counterion not detected).

Anal. Calcd. for $C_{30}H_35N_3O_6$ 1.25 HCl: C, 62.21; H, 6.31; N, 7.25. Found: C, 62.13; H, 6.25; N, 7.30.

7.5 EXAMPLE 4

Preparation of (t-Butyloxycarbonyl)glycyl-tyrosyl-(N-ϵ-benzyloxycarbonyl)lysine benzyl ester 5

A suspension of tyrosyl-lysine derivative 4 (13.69 g, 24.7 mmol) in $CH_2Cl_2$ (80 mL) was treated with diisopropylethylamine (4.3 mL, 24.7 mmol) and the resulting solution was cooled to 0° C. t-Butyloxycarbonyl glycine (Aldrich, 4.33 g, 24.7 mmol) was added in one portion, followed by 1-ethyl-3-(3-dimethylaminopropyl)carbodiimide (Sigma, 5.22 g, 27.2 mmol). The homogeneous solution was stirred 0° C. for one hour then stored at 5° C. After 18 h, the reaction solution was washed with saturated $NaHCO_3$, then 1N HCl, dried ($MgSO_4$), and concentrated to give a white solid: purity 95.4% (HPLC, System C); MP 127°-130° C.; $^1H$ NMR (DMSO-$d_6$)δ 1.29 (m, 4H),1.38 (s, 9H), 1.70 (m, 2H), 2.61 (m, 1H), 2.82 (m, 1H), 2.98 (m, 2H), 3.45 (m, 2H), 4.24 (m, 1H), 4.50 (m, 1H), 4.99 (s, 2H), 5.11 (s, 2H), 6.62 (d, J=8.5 Hz, 2H), 6.91 (m, 1H, exchangeable with $D_2O$), 7.39 (m, 10H), 7.85 (d, J=9.2 Hz, 1H, exchangeable with $D_2O$), 8.42 (d, J=7.7 Hz, 1H, exchangeable with $D_2O$), 9.19 (s, 1H, exchangeable with $D_2O$); $^{13}C$ NMR ($CDCl_3$) δ 22.0, 28.3, 29.7, 31.4, 36.9, 40.8, 44.5 , 52.3, 54.1, 67.0, 67.1, 80.6, 115.79, 127.0, 128.2, 128.5, 128.6, 130.4, 135.3, 136.3, 155.8 , 156.9, 169.7, 170.6, 171.4; FAB+ MS m/z 691 (M+H), 591 (M+H $Me_3CO_2C$).

Anal. Calcd. for $C_{37}H_{46}N_4O_9$: 64.32; H, 6.72; N, 8.11. Found: C, 64.16; H, 6.77; N, 8.08.

7.6 EXAMPLE 5

Preparation of (t-Butyloxycarbonyl)glycyl-tyrosyl-lysine 6

A solution of the glycyl-tyrosyl-lysine derivative 5 (16.80 g, 24.35 mmol) in warm ethanol (40° C., 750 mL) was treated with 10% Pd/C (Aldrich, 0.84 g) and $H_2$ gas was bubbled in with vigorous stirring for five hours. The catalyst was removed by filtration with the aid of Celite, and solvent was removed under vacuum. Drying under vacuum over $P_2O_5$ provided 10.38 g (91%) of a white solid. Recrystallization from ethanol returned 8.05 g. Purity: 96.0% (HPLC, System D); MP>200° C.; $^1H$ NMR (DMSO-$d_6$) δ 1.29 (m, 2H), 1.36 (s, 9H), 1.57 (m, 4H), 2.71 (m, 3H), 2.88 (m, 1H), 3.49 (m, 2H), 3.85 (m, 1H), 4.40 (m, 1H), 6.60 (d, J=8.3 Hz, 2H), 6.92 (m, 1H, exchangeable with $D_2O$); 7.86 (d, J=8.3 Hz, 1H, exchangeable with $D_2O$); $^{13}C$ NMR (DMSO-$d_6$) δ 22.0, 27.1, 28.0, 28.1, 31.8, 36.8, 43.1, 53.7, 54.1, 78.0 , 114.8, 127.5, 127.6, 128.3, 130.0, 155.6, 155.8, 169.0, 169, 174.0; FAB+ MS m/z 467 (M+H), 367 (M +H -$Me_3CO_2C$).

Anal. Calcd. for $C_{22}H_{34}N_4O_7$: C, 56.62; H, 7.35; N, 12.01. Found: C, 56.70; H, 7.35; N, 12.02.

7.7 EXAMPLE 6

Preparation of (t-Butyloxycarbonyl)glycyl-tyrosyl-(N-ε-diethylenetriamine-pentaacetic acid)lysine 7

Method A. A solution of N-hydroxysuccinimide (27.1 g, 235.8 mmol) in DMF (230 mL) was treated with DTPA dianhydride (42.1 g, 117.9 mmol) and warmed to 70° C. until all of the anhydride reacted and dissolved. The solution was cooled to rt, and a solution of (t-butyloxycarbonyl)glycyl-tyrosyl-lysine 6 (11.0 g, 23.60 mmol) in water (65 mL) was introduced. After 4 hr at rt, HPLC analysis indicated that starting tripeptide had been consumed. Excess dianhydride was destroyed and the resulting DTPA byproduct was removed by diluting the reaction mixture with MeOH (250 mL) and water (60 mL), stirring for 1 hr, and filtering. Solvents were removed by rotary evaporation and the residue was triturated with THF (2×300 mL) and MeCN (30 mL). This operation deposits the product as a white solid and removes residual DMF and most of the N-hydroxysuccinimide, leaving 19.0 g (95.6%) of a white solid. An analytical sample was prepared by three successive recrystallizations from methanol/isopropyl alcohol. Purity: 95.9% (HPLC, System B); MP 160° C. (decomposes over a large temperature range); $^1H$ NMR ($D_2O$) δ 1.2–1.8 (m, 15H), 2.9–4.0 (m, 24H), 4.29 (M, 1H), 4.59 (m, 1H), 6.81 (m, 2H), 7.12 (m, 2H); FAB+ MS m/z 842 (M+H), 742 (M+H - $Me_3CO_2C$).

7.8 EXAMPLE 7

Preparation of (t-Butyloxycarbonyl)glycyl-tyrosyl-(N-ε-diethylenetriamine-pentaacetic acid)lysine 7 from GYK-DTPA Method B. GYK-DTPA hydrochloride (12.87 g, 16.5 mmol) was dissolved in saturated $NaHCO_3$ (53 ml) and the pH was adjusted to about 8 with $Na_2CO_3$. A solution of di-t-butyl-dicarbonate (4.33 g, 19.8 mmol) in MeOH (33 ml) was added, and the solution was stirred at rt for 6 h. Solvents were removed by rotary evaporation, and the residue was chromatographed on a low-pressure C18 column. The product eluted with water, and was lyophilized to yield 12.5 g (90%) having a purity of 99% (HPLC, System B). $^1H$ NMR was identical to a sample prepared by Method A.

7.9 EXAMPLE 8

Preparation of glycyl-tyrosyl-(N-ε-diethylenetriaminepentaacetic acid) lysine 8

Method C. Crude Boc-GYK-DTPA 14 (3.60 g, 4.28 mmol) was dissolved in 1N NCl (48 mL) and incubated at rt for 7 h. HPLC (System E) indicated that about 3% starting urethane remained. The solution was stored at 5° C. for 15 h. NaCl (2.8 g) was added to make the solution 1N in salt. The pH was adjusted to 2.2 (10M NaOH) and the entire solution was then pumped onto a C18 column (Alltech Lobar, no metal fittings, 35 mm ID×170 mm). Salts were removed from the column by elution with 9 mM HCl (300 mL). GYK-DTPA was then eluted with 1 MeOH: 4 $H_2O$ which was 9 mM in HCl (2 l). Three fractions were collected, which upon lyophilization yielded 0.08 g (96% pure, 2.4% yield), 0.76 g (99% pure, 22.8% yield), and 1.07 g (90% pure, 32% yield). Purity was determined by HPLC (System E). The combined yield for the last two steps was 57%, with the purity of the combined fractions of final product 94%. MP 160° C. (decomposes over a large temperature range); $^1H$ NMR ($D_2O$). For assignments, refer to FIG. 2: δ 1.888 (m, 2H, Lys γ), 1.400 (m, 2H, Lys δ), 2.890 (AB of ABX, $^2J$=14 Hz, J=8.0, 7.0 Hz, 2H, Tyr β), 3.122 (m, overlapping resonances, 6H, Lys ε and DTPA F and G), 3.298 (m, 2H, DTPA H), 3.407 (m, 2H, DTPA E), 3.551 (s, 2H, DTPA D), 3.696 (AB, 2H, $^2J$=16.4 Hz, Gly α), 3.716 (s, 2H DTPA C), 3.818 (s, 4H, 2-DTPA B), 3.863 (s, 2H, DTPA A), 4.170 (dd, J=8.5, 8.2 Hz, 1H, Lys α), 4.512 (dd, J=8.0, 7.0 Hz, 1H Tyr α), 6.734 (d, J=8.4 Hz, 2H, 2 Tyr δ), 7.041 (d, J=8.4 Hz, 2H, 2 Tyr ε); $^{13}C$ NMR ($D_2O$) δ 25.0, 30.4, 33.0, 39.2, 42.0, 52.9, 53.4, 55.0, 55.1, 55.7, 57.3, 57.3, 58.0, 59.5, 59.8, 118.6, 131.0, 133.7, 157.8, 170.0, 173.7, 174.5, 175.8, 176.1, 178.5; FAB+ MS m/z 742 ($M^+$, Cl counterion not detected).

Anal. Calcd. for $C_{31}H_{48}ClN_7O_{14}$: C, 47.85; H, 6.22; N, 12.60. Found: C, 47.61; H, 6.22; N, 12.40.

7.10 EXAMPLE 9

Preparation of glycyl-tyrosyl-N-ε-diethylenetriaminepentaacetic acid) lysine 8

Method D. Boc-GYK-DTPA 7 (12.5 g, 14.3 mmol), prepared by Method B, was dissolved in 1N HCl (200 mL) and incubated at rt for 8 h. The solution was then lyophilized, providing 11.7 g (96.7%) of white powder. Purity: 99% (HPLC, System E). $^1$H NMR was identical to a sample prepared by Method C.

Crude GYK-DTPA may optionally be passed through a low-pressure glass C18 column.

It is possible that the column step be avoided if the penultimate intermediate is prepared in very high purity, e.g. by recrystallization There are therefore two methods of producing GYK-DTPA of acceptable purity by this approach: 1) attaining high purity in the penultimate intermediate by recrystallization, 2) purifying end product with low pressure C18 chromatography.

The Boc approach offers higher yield throughout, since there is no need for the high pressure liquid chromatographic purification at the end. The yields are high and product purification requires simple synthetic operations.

Several references have been cited in the specification, the entire disclosures of each of Which are incorporated by reference herein in their entirety.

What is claimed is:

1. A method for preparing a tripeptide-chelator comprising:

(a) reacting a N-ε-carbobenzyloxy lysine with benzyl alcohol in a solution of p-toluenesulfonic acid in toluene to form a carboxy protected N-ε-carbobenzyloxy lysine;

(b) reacting a tyrosine residue having a Boc-protecting group with said carboxy protect N-ε-carbobenzyloxy lysine in the presence of a suitable coupling agent selected from the group consisting of 1-ethyl-3(3-dimethylamino propyl)-carbodiimide, benzotriazol-1-yloxytris (dimethylamino)phosphonium hexafluorophosphate and dicyclohexylcarbodiimide to form a Boc-tyrosine (N-ε-CBZ) lysine ester dipeptide having a Boc protected amine terminus and a carboxy terminus protected as an ester;

(c) removing said Boc protecting group from said Boc protected amine terminus by treatment with an acid effective to form an acid salt of said dipeptide, said acid being in a suitable solvent selected from the group of toluene, ethylacetate, methanol, ethanol, isopropyl alcohol, dioxane, dimethoxyethane, dimethylformanide, methylene chloride and tetrahydrofuran;

(d) reacting a glycine residue having a Boc-protecting group with said acid salt of the dipeptide in the presence of a suitable coupling agent selected from the group consisting of 1-ethyl-3(3-dimethylamino propyl)carbodiimide, benzotriazol-1-yloxytris (dimethylamino) phosphonium hexafluorophosphate and dicyclohexylcarbodiimide to form a tripeptide having a Boc-protected amine terminus and a protected carboxy terminus;

(e) reacting said tripeptide with a hydrogen gas in the presence of a suitable catalyst selected from the group consisting of pallidum on carbon, platinum on carbon and platinum oxide in a solvent selected from the group consisting of methanol and ethanol to remove protecting groups from both the lysine side chain and the carboxy terminus to form a partially deprotected tripeptide;

(f) reacting said partially deprotected tripeptide with DTPA-disuccinimdyl ester to form a Boc-protected GYK-DTPA; and (g) reacting asid Boc-protected GYK-DTPA with an acid to remove said Box protecting group from said Boc protected amine terminus to form GYK-DTPA in the acid salt form.

2. A method of preparing a tripeptide-chelator comprising:

(a) reacting a tyrosine residue having a Boc-protecting group with a carboxy protected N-ε-carbobenzyloxy lysine in the presence of 1-ethyl-3-(3-dimethylaminopropyl)-carbodiimide to form a dipeptide Boc-tyrosine (N-ε-CBZ) lysine ester having a Boc protected amine terminus and an ester protected carboxy terminus;

(b) removing said Boc protecting group from said Boc-protected amien terminus by treatment with hydrogen chloride in ethyl acetate to form a hydrochloride salt of said dipeptide;

(c) reacting a glycine residue having a Boc-protecting group with said hydrochloride salt of the dipeptide in the presence of 1-ethyl-3-(3-dimethylaminopropyl)-carbodiimide to form a tripeptide having a Boc-protected amine terminus;

(d) reacting asid tripeptide with hydrogen gas in the presence of palladium on carbon in an ethanol solvent to from a tripeptide containing a Boc protecting group at the amine terminus;

(e) reacting said tripeptide with diethylenetriaminepentaacetic disuccinimdyl ester to form a Boc protected GYK-DTPA; and (f) reacting said Boc protected GYK-DTPA with aqueous HCl to remove said Boc-protecting group to form a GYK-DTPA or GYK-DTPA HCl.

* * * * *